United States Patent [19]

Welch

[11] Patent Number: 4,620,053
[45] Date of Patent: Oct. 28, 1986

[54] ZINC ALUMINATE DOUBLE BOND ISOMERIZATION CATALYST AND DOUBLE BOND ISOMERIZATION OF OLEFINS EMPLOYING SAID CATALYST

[75] Inventor: M. Bruce Welch, Bartlesville, Okla.

[73] Assignee: Phillips Petroleum Company, Bartlesville, Okla.

[21] Appl. No.: 745,556

[22] Filed: Jun. 17, 1985

[51] Int. Cl.$^4$ ............................................. C07C 5/23
[52] U.S. Cl. ..................................... 585/664; 585/666; 585/667; 585/671; 502/342; 502/355
[58] Field of Search ............... 585/664, 666, 667, 670, 585/671; 502/342, 341, 355

[56] References Cited

U.S. PATENT DOCUMENTS

| | | | |
|---|---|---|---|
| 2,623,020 | 12/1952 | Gilbert et al. | 502/307 |
| 2,786,037 | 3/1957 | Gladrow et al. | 502/342 |
| 2,822,336 | 2/1958 | Poleck | 502/307 |
| 2,846,365 | 8/1958 | Gladrow | 502/307 |
| 3,340,317 | 9/1967 | Kenton | 585/377 |
| 3,413,083 | 11/1968 | Daepdliker | 423/263 |
| 3,449,463 | 6/1969 | Kenton et al. | 585/600 |
| 3,546,313 | 12/1970 | Banks | 585/643 |
| 3,660,507 | 5/1972 | Reusser | 585/374 |
| 3,674,706 | 7/1972 | Box et al. | 502/25 |
| 3,707,579 | 12/1972 | Montgomery | 585/643 |
| 3,729,524 | 4/1973 | Reusser | 585/329 |
| 3,766,291 | 10/1973 | Drehman | 585/321 |
| 3,786,112 | 1/1974 | Reusser et al. | 585/644 |
| 3,823,088 | 7/1974 | Box et al. | 502/342 |
| 3,915,897 | 10/1975 | Reusser et al. | 502/241 |
| 3,959,208 | 5/1976 | Baskin | 523/153 |
| 4,041,099 | 8/1977 | Hutson | 585/434 |
| 4,064,190 | 12/1977 | Eastman et al. | 585/848 |
| 4,167,472 | 9/1979 | Dick et al. | 585/419 |
| 4,180,524 | 12/1979 | Reusser | 585/644 |
| 4,215,017 | 7/1980 | Reusser | 502/210 |
| 4,260,845 | 4/1981 | Shioyama | 585/640 |

Primary Examiner—Andrew H. Metz
Assistant Examiner—A. Pal
Attorney, Agent, or Firm—William R. Sharp

[57] ABSTRACT

A double bond isomerization catalyst is provided which consists essentially of zinc aluminate. A process for the double bond isomerization of olefinic feedstocks using this catalyst is also disclosed.

6 Claims, No Drawings

4,620,053

ZINC ALUMINATE DOUBLE BOND ISOMERIZATION CATALYST AND DOUBLE BOND ISOMERIZATION OF OLEFINS EMPLOYING SAID CATALYST

This invention relates to a process for producing an activated zinc aluminate ($ZnAl_2O_4$) double bond isomerization catalyst. In another aspect, the invention relates to the catalyst produced according to the above process. According to yet another aspect, the invention relates to a process of double bond isomerizing olefins using such an activated catalyst.

In the upgrading of olefins or the conversion of one or more olefins to a more desirable olefin or mixture of olefins, it frequently has been necessary to treat the olefins for double bond isomerization. Double bond isomerization can be simply defined as the shifting of a double bond from one position in an olefin to another position in the olefin.

One example of a double bond isomerization application is in conjunction with disproportionation processes. It has been found that the use of a catalyst which possesses double bond isomerization activity in a disproportionation process is advantageous in that it increases the rate of conversion and makes possible the production of a wider range of reaction products. For example, the presence of such double bond isomerization activity greatly increases the disproportionation rate of symmetrical olefins such as butene-2. An additional example involves the preparation of synthetic lubricants from heavy olefins with the first step being the double bond isomerization of heavy olefins to internal olefins.

Heretofore, magnesium oxide (MgO) has been the most commonly used double bond isomerization catalyst. Although the double bond isomerization activity of magnesium oxide is adequate for most purposes, further development and improvement would be desirable.

SUMMARY OF THE INVENTION

It is, therefore, an object of the present invention to provide an improved double bond isomerization catalyst and process for its production.

It is also an object of the invention to provide a process of double bond isomerizing olefins employing such an improved catalyst.

Certain of the above objects are realized in a process for the double bond isomerization of an olefinic feedstock having at least four carbon atoms per molecule which comprises the step of contacting the olefinic feedstock under effective double isomerization conditions with an activated catalyst composition consisting essentially of zinc aluminate.

According to another aspect of the invention, there is provided a process of preparing an activated double bond isomerization catalyst from a composition consisting essestially of zinc aluminate which includes the steps of: calcining the composition in an oxygen containing atmosphere at a temperature of about 250° C. to about 800° C. for a time of about 1 to about 30 hours; and contacting the calcined composition with a reducing gas selected from the group consisting of carbon monoxide, nitric oxide, and hydrogen at a temperature of about 400° C. to about 750° C. for a time in the range of about 1 minute to about 30 hours. According to one embodiment, the zinc aluminate composition is also treated with water.

According to yet another aspect of the invention, an activated double bond isomerization catalyst is provided which is produced according to the above described process.

The inventive double bond isomerization catalyst is highly effective in double bond isomerizing olefinic feedstocks, and has been shown to achieve up to over 80% conversion in certain experimental examples which will follow. Moreover, a zinc aluminate catalyst employed according to the invention has been shown to achieve double bond isomerization conversion percentages at least comparable with and more often in excess of those achieved with magnesium oxide under comparable reaction conditions.

DETAILED DESCRIPTION OF THE INVENTION

Preferred embodiments of the invention will now be described in terms of two basic parts: process of preparing the catalyst; and process of double bond isomerizing olefins using the catalyst.

PROCESS OF PREPARING THE ACTIVATED CATALYST

The starting material in the process is a composition which essentially consists of zinc aluminate ($ZnAl_2O_4$) prepared by any conventional technique. Commercially available samples of zinc aluminate are quite suitable for use in the present invention. The zinc aluminate can range in form from fine powder to coarse granules, and more specifically, can take the form of agglomerates, pellets, spheres, extrudates, beads, and the like, depending upon the type of contacting technique which utilizes the finished catalyst. Preferably, the zinc aluminate should have a surface area of at least about 1 square meter per gram.

The zinc aluminate can optionally be treated with water as follows. The zinc aluminate sample is placed in a suitable container and covered with water. It is suggested that about 5 to about 20 mL of water, preferably deionized, be added per gram of zinc aluminate. The water is allowed to contact the zinc aluminate at a temperature of at least about 20° C. for at least about 0.1 hour, and most preferably at a temperature of about 50° C. to about 150° C. for a time of about 1 hour. Most conveniently, this contacting step is carried out at atmospheric pressure. The zinc aluminate is then recovered by any suitable technique such as decanting and/or filtering, or by heating unitl all of the water evaporates.

After such water treatment, the zinc aluminate is preferably dried in an appropriate oven at about 250° C. for sufficient time to achieve acceptable dryness, such as about 1 or 2 hours. It should be noted that even if the zinc aluminate is not water treated as described above, it is preferred that it be dried before subsequent steps are carried out.

Next, the zinc aluminate is calcined by heating in an oxygen containing atmosphere, preferably air, at a temperature of about 250° C. to about 800° C. for about 1 hour to about 30 hours, most preferably at a temperature of about 300° C. to about 650° C. This calcining-oxygen treatment step is most conveniently performed by placing the zinc aluminate in the reactor and passing a continuous flow of air through the reactor.

After calcination, the zinc aluminate is preferably treated with a reducing gas such as carbon monoxide (CO), nitric oxide (NO) or hydrogen ($H_2$). The zinc aluminate is contacted with the reducing gas, most preferably with a continuous flow thereof, at a temperature in the range of about 400° C. to about 750° C. for a period of time ranging from about 1 minute to about 30 hours, and most preferably at a temperature of about 500° C. to about 650° C. for a time of about 15 minutes to about 1 hour.

After such reducing gas treatment, the zinc aluminate is preferably flushed with an inert gas such as argon. If desired, the zinc aluminate could also be flushed with the inert gas in a similar manner immediately before the reducing gas treatment.

Zinc aluminate as treated above is activated (i.e. catalytically active), and is ready for use as a double bond isomerization catalyst for the double bond isomerization of olefin feedstocks.

DOUBLE BOND ISOMERIZATION PROCESS

Suitable olefinic feedstocks for a double bond isomerization process according to the invention include acyclic and cyclic mono- and polyenes having at least 4 carbon atoms per molecule including alkyl and aryl derivatives thereof, and mixtures of the above olefins.

Some specific olefinic feedstocks suitable for use with the invention are set forth below, these feedstocks being given only by way of example. Moreover, the feedstocks listed are not only capable of being double bond isomerized, but are also capable of being disproportionated. As noted above, in a typical application, the feedstock might be subjected to disproportionation following double bond isomerization.

Some specific examples of acyclic olefin feedstocks suitable for isomerization in accordance with the invention include 1-butene, 2-butene, 1-pentene, 2-pentene, isoprene, 1-hexene, 1,4-hexadiene, 2-heptene, 1-octene, 2,5-octadiene, 2-nonene, 1-dodecene, and the like, and mixtures thereof.

Some specific examples of cyclic olefin feedstocks are cyclobutene, cyclopentene, cyclohexene, 3-methylcyclopentene, 4-ethylcyclohexene, 4-benzylcyclohexene, cyclooctene, and the like and mixtures thereof.

The olefinic feedstock is double bond isomerized by contact with activated zinc aluminate catalyst under effective double bond isomerization conditions in either a batch-wise or continuous process. The double bond isomerization activity of the inventive catalyst is ideally suited for use in a continuous reaction. Types of reactors useable in the isomerization process include fixed bed reactors, fluidized bed reactors, suspended catalyst systems, and the like.

The reaction conditions can vary considerably, depending, for example, on the proportions and reactivities of the olefin reactants. Contacting temperatures can range widely so long as effective for the desired double bond isomerization conversion. Exemplary temperatures presently are considered to be in the range of about 50° C. to about 600° C., most preferably about 150° C. to about 550° C. The contacting pressures can also range widely as long as effective. By way of example, a pressure in the range of 0 p.s.i.g. to several hundred p.s.i.g. will generally be effective.

In a continuous process, the feed rate can vary according to the feedstock being used and the desired degree of conversion but generally will be in the range of about 0.1 to about 1,000 weight of olefin per weight of catalyst per hour (w./w./hr.), or weight hourly space velocity (WHSV), of feed olefin over the catalyst, preferably about 10 to about 100, in order to obtain an optimum balance of conversion yield, efficiency, and convenience.

In batch operations, the reaction time can vary as convenient, from such as about 0.01 to about 24 hours, preferably about 0.1 to about 5 hours.

Effluent from the reactor includes a double bond isomerized olefin. The extent of double bond isomerization of the feedstock in terms of conversion percentages will become more apparent in illustrative examples which follow. Generally speaking, the degree of double bond isomerization achieved by the invention is at least comparable to or better than conversion with prior art magnesium oxide catalysts, depending on isomerization conditions and the nature of the catalyst preparation process. Best results are obtained employing reducing gas and water treatment in the catalyst preparation process. If a diluent is used in the process, the desired isomerized product can be separated from the diluent by conventional means, such as distillation.

Spent zinc aluminate catalyst can be recovered and regenerated by calcining in an oxygen containing atmosphere and treatment with a reducing gas in a manner similar to that previously described.

Several examples will now be set forth to assist one skilled in the art in a further understanding of the invention, but should not be construed to limit the invention in any manner. All percentages given are weight percentages.

EXAMPLE I (control)

0.90 grams of 9–20 mesh magnesium oxide was placed in a beaker and covered with distilled water. Then, 15.7 mL of $NH_4OH$ was added, the resulting mixture being heated at 80° C. for 2 hours. The magnesium oxide was then rinsed several times in distilled water and dried overnight in a vacuum oven at 100° C. For activation, 0.71 grams of the magnesium oxide was heated in air at 550° C. for 2 hours in a tubular steel fixed bed reactor. The reactor contents were then treated with flowing carbon monoxide at 550° C. for 30 minutes, followed by cooling with a flow of argon.

A continuous flow of 1-hexene was passed through the above prepared catalyst at various temperatures and weight hourly space velocities (WHSV) according to seven different runs, each run being carried out at a pressure of 50 p.s.i.g. The effluent, on analysis by gas chromatography, was found to contain olefins as shown and in the quantities indicated in the following Table IA.

TABLE IA

| Run | 1 | 2 | 3 | 4 | 5 | 6 | 7 |
|---|---|---|---|---|---|---|---|
| Temperature (°C.) | 201 | 299 | 348 | 348 | 401 | 398 | 450 |
| WHSV (w./w./hr.) | 20 | 40 | 40 | 80 | 41 | 79 | 84 |
| % 1-$C_6$ | 46.71 | 40.56 | 30.80 | 53.65 | 29.53 | 50.12 | 40.72 |
| % trans 2 & 3 $C_6$ | 26.49 | 35.31 | 44.86 | 28.32 | 46.36 | 30.59 | 37.80 |
| % cis 2-$C_6$ | 26.05 | 24.03 | 24.27 | 17.97 | 24.02 | 19.21 | 21.39 |
| % total conversion | 52.54 | 59.34 | 69.13 | 46.29 | 70.38 | 49.80 | 59.19 |

The "total" conversion percentage as calculated in Table IA is simply the sum of the trans 2 and 3-hexene and cis 2-hexene conversion percentages.

The sample produced according to run number 3 was hydrogenated so as to form saturated hydrocarbons (i.e. hexane, isomers of hexane, and others). The resulting product was analyzed by mass spectometry to reveal the extent of skeletal isomerization. The results are shown in Table IB:

TABLE IB

| Run | 3 |
|---|---|
| % Lights (<$C_6$) | — |
| % 2-methyl-pentane | — |
| % 3-methyl-pentane | 1.17 |
| % n-hexane | 98.75 |
| % heavies (>$C_6$) | 0.06 |

The presence of measurable quantities of 3-methyl-pentane, an isomer of hexane having skeletal branching, indicates that the magnesium oxide catalyst does have some skeletal isomerization activity in addition to double bond isomerization activity. The very small quantity of heavy hydrocarbons indicate that some oligomerization and polymerization has taken place.

EXAMPLE II (invention)

5 grams of zinc aluminate extrudate was placed in a beaker with 50 ml of deionized water. The beaker was placed on a hot plate and heated at a temperature of 90° C. for 1 hour until all of the water evaporated. The zinc aluminate was then dried in a muffle oven at 250° C. for 1 hour. 0.71 grams of the dried zinc aluminate was placed in a tubular steel fixed bed reactor. The reactor and contents were heated for 2 hours in flowing air at 550° C. The reactor contents were then treated with flowing carbon monoxide for 30 minutes, also at 550° C. The resultant activated catalyst was cooled with argon as in Example I.

Seven runs were performed with the above prepared catalyst with a continuous flow of 1-hexene feedstock under WHSV and temperature conditions comparable to those in Example I, each run being performed at 50 psig. Results are shown in Table IIA.

TABLE IIA

| Run | 8 | 9 | 10 | 11 | 12 | 13 | 14 |
|---|---|---|---|---|---|---|---|
| Temperature (°C.) | 201 | 299 | 350 | 349 | 400 | 401 | 450 |
| WHSV (w./w./hr.) | 20 | 41 | 40 | 79 | 40 | 80 | 79 |
| % 1-$C_6$ | 50.62 | 35.32 | 37.20 | 69.58 | 37.54 | 62.87 | 58.22 |
| % trans 2 & 3-$C_6$ | 27.08 | 42.03 | 40.60 | 18.17 | 39.55 | 22.54 | 26.23 |
| % cis 2-$C_6$ | 21.21 | 22.53 | 22.08 | 12.20 | 22.76 | 14.50 | 15.36 |
| % total conversion | 48.29 | 64.56 | 62.68 | 30.37 | 62.31 | 37.04 | 41.59 |

Conversion percentages can be seen to range from about 30% to about 65%.

The products obtained according to run numbers 9, 10 and 11 were hydrogenated and analyzed as in Example I. Results are given in Example IIB.

TABLE IIB

| Run | 9 | 10 | 11 |
|---|---|---|---|
| Lights (<$C_6$) | 0.01 | 0.10 | 0.02 |
| 2-methyl-pentane | — | 0.01 | 0.01 |
| 3-methyl pentane | 1.19 | 1.21 | 1.23 |
| n-hexane | 98.77 | 98.62 | 98.69 |
| heavies (>$C_6$) | 0.03 | 0.06 | 0.05 |

The above data shows that only a very small percentage (<2%) of the product are isomers of hexane having skeletal branching. This indicates that substantially all of the isomerization activity of the catalyst of this example is double bond isomerization activity. These results compare favorably with the Control Example.

EXAMPLE III (invention)

5 grams of zinc aluminate was placed in a muffle furnace at 250° C. for 1 hour. After this treatment, 0.71 grams of the zinc aluminate was placed in a tubular steel fixed bed reactor. Reactor contents were heated for 2 hours in flowing air at 550° C., and then treated 30 minutes in a flow of carbon monoxide at a temperature of 550° C. as in Example II. The activated catalyst thus obtained was cooled with argon gas.

Seven additional runs were made wherein 1-hexene was passed through the above prepared catalytic section under the same pressure conditions as employed in Example II. Results are given in Table IIIA.

TABLE IIIA

| Run | 15 | 16 | 17 | 18 | 19 | 20 | 21 |
|---|---|---|---|---|---|---|---|
| Temperature (°C.) | 204 | 298 | 347 | 350 | 397 | 400 | 448 |
| WHSV (w./w./hr.) | 19 | 41 | 41 | 79 | 41 | 80 | 81 |
| % 1-$C_6$ | 30.88 | 19.66 | 15.43 | 34.90 | 19.66 | 46.07 | 51.32 |
| % trans 2 & 3-$C_6$ | 46.88 | 57.99 | 61.09 | 43.88 | 56.85 | 34.65 | 30.80 |
| % cis 2-$C_6$ | 22.16 | 22.22 | 23.25 | 21.09 | 23.20 | 19.18 | 17.60 |
| % Total conversion | 69.04 | 80.21 | 84.34 | 64.97 | 80.05 | 53.83 | 48.40 |

It can be seen from Table IIIA that total conversion percentages range from just under 50% to over 80%, and in most runs exceed the conversion percentages obtained with magnesium oxide under comparable conditions.

Analysis for skeletal isomerization is shown in Table IIIB for the product in runs 16 and 17.

TABLE IIIB

| Runs | 16 | 17 |
|---|---|---|
| % Lights (<$C_6$) | 0.04 | 0.01 |
| % 2-methyl-pentane | — | 0.02 |
| % 3-methyl-pentane | 1.17 | 1.19 |
| % n-hexane | 98.74 | 98.76 |
| % heavies (>$C_6$) | 0.05 | 0.02 |

The above data again shows that very little skeletal isomerization has taken place.

EXAMPLE IV (invention)

5 grams of zinc aluminate extrudate was placed in a muffle furnace and heated at 250° C. for 1 hour. After such heat treatment, 0.71 grams of the zinc aluminate was placed in a tubular steel fixed bed reactor. The reactor and contents were heated for 2½ hours in flowing air at 550° C. The resulting activated catalyst was cooled under a flow of argon gas as in the previous Examples.

Seven runs were performed with the above prepared catalyst with a continuous flow of 1-hexene feedstock under WHSV and temperature conditions comparable to those employed in Examples I, II and III. Results are shown in Table IVA.

TABLE IVA

| Run | 22 | 23 | 24 | 25 | 26 | 27 | 28 |
|---|---|---|---|---|---|---|---|
| Temperature (°C.) | 203 | 300 | 350 | 351 | 399 | 402 | 449 |
| WHSV (w./w./hr.) | 20 | 40 | 41 | 82 | 40 | 79 | 80 |
| % 1-$C_6$ | 33.20 | 21.49 | 16.76 | 33.60 | 34.08 | 59.31 | 60.10 |
| % trans 2 & 3-$C_6$ | 44.17 | 55.28 | 59.45 | 44.88 | 45.80 | 26.52 | 25.86 |
| % cis 2-$C_6$ | 22.22 | 23.07 | 23.56 | 21.37 | 19.76 | 14.06 | 13.77 |
| % total conversion | 66.39 | 78.35 | 83.01 | 66.25 | 65.56 | 40.58 | 39.63 |

The above data shows that 1-hexene was effectively double bond isomerized with total conversion percentages ranging from about 40% to about 83%.

Results of skeletal isomerization analysis of the product from run number 24 after hydrogenation are shown in Table IVB.

TABLE IVB

| Run | 24 |
| --- | --- |
| % Lights (<$C_6$) | 0.01 |
| % 2-methyl-pentane | 0.01 |
| % 3-methyl-pentane | 1.19 |
| % n-hexane | 98.76 |
| % heavies (>$C_6$) | 0.03 |

Obviously many modifications and variations of the present invention are possible in light of the above teachings. It is therefore to be understood that within the scope of the appended claims the invention may be practiced otherwise than as specifically described.

That which is claimed is:

1. A process for the double bond isomerization of an olefinic feedstock having at least four carbon atoms per molecule comprising:

contacting said olefinic feedstock under effective double bond isomerization conditions with an activated catalyst composition consisting essentially of zinc aluminate.

2. A process as recited in claim 1, wherein said contacting step is carried out a temperature of about 50° C. to about 600° C.

3. A process as recited in claim 2, wherein said contacting step is carried out at a temperature of about 150° C and about 500° C.

4. A process for double bond isomerizing an olefinic hydrocarbon feedstock having at least four carbon atoms per molecule, said process comprising:

contacting said olefinic feedstock with an activated catalyst prepared by calcining a composition which essentially consists of zinc aluminate in an oxygen containing atmosphere at a temperature of about 250° C. to about 800° C. for a time of about 1 hour to about 30 hours and then contacting the thus calcined composition with a reducing gas selected from the group consisting of carbon monoxide, nitric oxide, and hydrogen at a temperature of about 400° C. to about 750° C. for a time of about 1 minute to about 30 hours, said activated catalyst contacting said olefinic feedstock under effective isomerization conditions to produce a double bond isomerized olefinic product.

5. A process as recited in claim 4, wherein preparation of said activated catalyst further comprises the steps of contacting said composition before said calcining step with a quantity of water at a temperature of at least about 20° C. for a time of at least about 0.1 hour; and recovering said composition.

6. A process as recited in claim 5 wherein said calcining of said composition is carried out at a temperature of about 300° C. to about 650° C., and wherein said reducing gas contacting step is carried out at a temperature of about 500° C. to about 650° C.

* * * * *